(12) United States Patent
Theron et al.

(10) Patent No.: US 9,695,674 B2
(45) Date of Patent: Jul. 4, 2017

(54) SUBSEA DOSING PUMP

(71) Applicant: ONESUBSEA IP UK LIMITED, London (GB)

(72) Inventors: Bernard E. Theron, Aberdeen (GB); Malcolm Atkinson, Aberdeen (GB)

(73) Assignee: ONESUBSEA IP UK LIMITED, London (GB)

( * ) Notice: Subject to any disclaimer, the term of this patent is extended or adjusted under 35 U.S.C. 154(b) by 71 days.

(21) Appl. No.: 14/245,763

(22) Filed: Apr. 4, 2014

(65) Prior Publication Data

US 2015/0285036 A1 Oct. 8, 2015

(51) Int. Cl.

| F04B 23/02 | (2006.01) |
| E21B 41/00 | (2006.01) |
| E21B 41/02 | (2006.01) |
| F04B 9/04 | (2006.01) |
| F04B 47/06 | (2006.01) |
| G01N 1/12 | (2006.01) |

(52) U.S. Cl.
CPC .......... *E21B 41/0007* (2013.01); *E21B 41/02* (2013.01); *F04B 9/047* (2013.01); *F04B 47/06* (2013.01); *G01N 1/12* (2013.01)

(58) Field of Classification Search
CPC ....... E21B 41/0007; F04B 13/00; F04B 49/06
USPC ............. 166/338; 417/20, 44.1, 212; 137/13
See application file for complete search history.

(56) References Cited

U.S. PATENT DOCUMENTS

| 7,204,679 B2* | 4/2007 | Wheeler | B24B 37/04 417/390 |
| 2006/0231265 A1* | 10/2006 | Martin | B63C 11/52 166/365 |
| 2015/0247493 A1* | 9/2015 | Theron | F04B 35/008 417/53 |

OTHER PUBLICATIONS http://www.longerpump.com/product/product204.html, accessed: May 15, 2014, 2 pages.
http://www.isco.com/products/products1.asp?PL=105, accessed: May 15, 2014, 1 page.

* cited by examiner

*Primary Examiner* — Matthew R Buck
*Assistant Examiner* — Patrick Lambe
(74) *Attorney, Agent, or Firm* — Conley Rose, P.C.

(57) ABSTRACT

A system is described for injecting small controlled amounts of fluid, such as de-emulsifier, into a flowing line at high pressure, in a high-pressure environment such as a subsea environment. The system is connected to the flowing line by tubing lines. It is enclosed either in a high-pressure vessel able to withstand high external pressure or in a vessel that is pressure-matched with the environment. The system is able to inject a controlled volume of fluid into the flowing line at relatively low injection rates.

25 Claims, 3 Drawing Sheets

SUBSEA DOSING PUMP

FIELD

The present disclosure relates generally to subsea fluid processing equipment. More particularly, the present disclosure relates to subsea deployable systems and methods for injecting fluid into a flow line at low injection rates.

BACKGROUND

When sampling in a subsea production line where several phases (oil, water, and/or gas) are flowing and only a specific phase is wanted, the sampling process relies on an ability to separate the phases and keep the desired phase while rejecting the unwanted phases. The phase separation can be achieved in a separator or elsewhere. However, in some instances, the phase separation is very difficult to perform within a reasonable amount of time, particularly when the phases are mixed as an emulsion. In such cases, de-emulsifying additives can be added to the mixture to carry out the separation. The amount of de-emulsifier is typically relatively small, on the order of several ppm, and should be added continuously into the flow. The injection pressure is high, typically the well pressure. In subsea operations the pump is immersed in a deep-sea environment.

SUMMARY

According to some embodiments, robust systems and methods are described for injecting chemical fluids, such as a de-emulsifier, into a sampling line connected to a high pressure subsea production line.

According to some embodiments, a subsea deployable pumping system is described. The system includes: a housing configured to be deployed in a subsea environment; a pump disposed within the housing the pump being configured to inject an injection fluid through an injection port; a pump driving mechanism disposed within the housing configured to drive the pump and cause the pump to inject the injection fluid, the pump and pump driving mechanism being configured to inject the injection fluid at a controllable rate less of less than 10 milliliters per minute; and a reservoir in fluid communication with the pump, configured to contain a volume of the injection fluid and to supply the injection fluid to the pump.

According to some embodiments, the pump includes: a cylindrical cavity in fluid communication with the injection port and the reservoir; and a plunger configured to fit tightly within the cylindrical cavity such that injection fluid within the cylindrical cavity is forced through the injection port when the plunger is driven in a longitudinal direction by the pump driving mechanism. According to some embodiments, the pump driving mechanism includes: a stepper motor configured to controllably rotate a drive shaft; and a driving linkage configured to drive the plunger in the longitudinal direction through the cylindrical cavity. The driving linkage can include: a screw configured to engage threads on the piston; and a gear system configured to allow the screw to be rotationally driven by the stepper motor through the drive shaft.

According to some embodiments, the housing is filled with a liquid, such as oil, and the system also includes a pressure compensator configured to match pressure of the liquid with seawater pressure outside the housing. The pressure compensator can include a piston separating two volumes, one of which is open to seawater outside the housing. The reservoir can include a pressure compensation mechanism configured to match pressure of the injection fluid within the reservoir, with seawater pressure outside the housing. According to some other embodiments, the housing is configured to maintain near atmospheric pressure within the housing while the exterior of the housing is exposed to subsea pressures. According to some embodiments, the pump and driving mechanism is configured to inject the injection fluid at pressures of at least 1000 psi.

According to some embodiments, the subsea pumping system is configured to be ROV deployable with equipment for exploration and production of hydrocarbon bearing fluid from subterranean reservoirs. In some examples, the injection fluid is a de-emulsifying agent and the subsea pumping system is configured for injection of the de-emulsifying agent into a multiphase flow line so as to aid in phase separation for fluid sampling purposes. In other examples, the injection fluid is used as an additive for measuring fluid flow rate (such as using a tracer substance) or for measuring a chemical property of a fluid flowing in a flow line (such as re-agents used for in-situ analysis).

According to some embodiments a subsea deployable pumping system is described. The system includes: a housing configured to be deployed in a subsea environment; a reservoir configured to contain a volume of injection fluid; a cylindrical cavity disposed within the housing in fluid communication with an injection port and with the reservoir; a plunger disposed within the housing configured to fit tightly within the cylindrical cavity such that injection fluid in the cylindrical cavity is forced through the injection port when the plunger is driven in a longitudinal direction; and a plunger driving mechanism disposed within the housing configured to drive the plunger in the longitudinal thereby injecting the injection fluid through the injection port.

According to some embodiments, a method is described for injecting small volumes of an injection fluid into a subsea flow line carrying a production fluid. The method includes: deploying a pumping system to a subsea location where a flow line is used to carry a flowing production fluid; and injecting the injection fluid into a fluid flow line using the pumping system, the injection fluid being injected at a rate of less than 10 milliliters per minute. According to some embodiments, the production fluid is a multiphase fluid, the injection fluid is a de-emulsifying agent, and the method further includes: separating a desired phase of the multiphase fluid at least in part aided by the injection of the de-emulsifying agent; and obtaining a sample of the desired phase of the multiphase fluid.

These together with other aspects, features, and advantages of the present disclosure, along with the various features of novelty, which characterize the invention, are pointed out with particularity in the claims annexed to and forming a part of this disclosure. The above aspects and advantages are neither exhaustive nor individually or jointly critical to the spirit or practice of the disclosure. Other aspects, features, and advantages of the present disclosure will become readily apparent to those skilled in the art from the following description of exemplary embodiments in combination with the accompanying drawings. Accordingly, the drawings and description are to be regarded as illustrative in nature, and not restrictive.

BRIEF DESCRIPTION OF THE DRAWINGS

To assist those of ordinary skill in the relevant art in making and using the subject matter hereof, reference is

DETAILED DESCRIPTION

In the following detailed description of the preferred embodiments, reference is made to accompanying drawings, which form a part hereof, and within which are shown by way of illustration specific embodiments by which the invention may be practiced. It is to be understood that other embodiments may be utilized and structural changes may be made without departing from the scope of the invention.

The particulars shown herein are by way of example and for purposes of illustrative discussion of the embodiments of the present invention only, and are presented in the cause of providing what is believed to be the most useful and readily understood description of the principles and conceptual aspects of the present invention. In this regard, no attempt is made to show structural details of the present invention in more detail than is necessary for the fundamental understanding of the present invention; the description taken with the drawings making apparent to those skilled in the art how the several forms of the present invention may be embodied in practice. Further, like reference numbers and designations in the various drawings indicate like elements.

According to some embodiments, a system is described for injecting small controlled amounts of fluid, such as de-emulsifier, into a flowing line at high pressure, in a high-pressure environment such as a subsea environment. The system is connected to the flowing line by tubing lines. It is enclosed either in a high-pressure vessel able to withstand high external pressure or in a vessel that is pressure-matched with the environment. The system is able to inject controlled volumes of fluid into the flowing line at relatively low injection rates.

Figure 1:
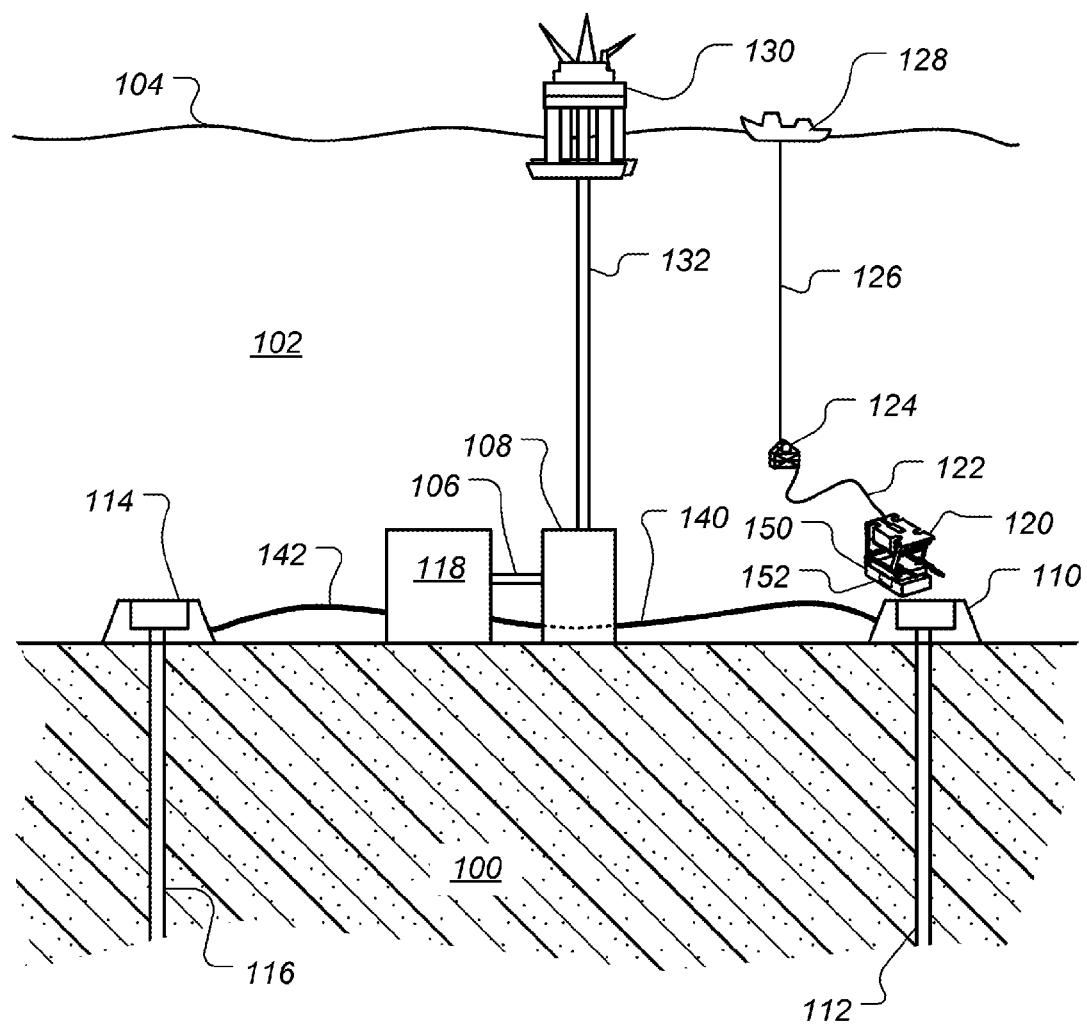
FIG. 1 is a schematic representation of a subsea production setting with which some of the dosing pump systems and methods described herein can be used, according to some embodiments.

FIG. 1 is a schematic representation of a subsea production setting in which some of the dosing pump systems and methods described herein can be used, according to some embodiments. Two wells, 112 and 116, are being used to extract production fluid from subterranean formation 100. The produced fluids from wells 112 and 116 move into manifold 118 from wellheads 110 and 114 via sea floor pipelines 140 and 142 respectively. The production fluid flows from manifold 118 to a subsea station 108 via pipeline 106, and then upwards through flowline 132 to a surface production platform 130 on the sea surface 104 of seawater 102. An intervention vessel 128 is shown deploying an ROV 120 via main lift umbilical 126, tether management system 124 and free-swimming tether 122. A subsea fluid sampling system 150 is shown attached as a skid to ROV 120.

Using ROV 120, the subsea sampling system 150 is shown being deployed at wellhead 110 of well 112. Although shown at a wellhead 110, according to some embodiments the sampling system 150, including dosing pump system 152, could be deployed at other subsea locations such as at the various flow lines 140, 142, 106 and 132, at manifold 118 and/or at subsea fluid processing station 108. According to some embodiments, rather than be ROV deployable, the sampling system 150, including the dosing pump system 152, could be integrated into equipment such as in wellhead 110, manifold 118 and/or subsea fluid processing station 108.

When sampling using subsea sampling system 150 in a subsea flow line (such as on wellhead 110, or in other locations described supra), often there are several phases (oil, water, and/or gas) flowing and only a specific phase is desired. Phase separation can be achieved in a separator within sampling system 150. In some instances, the phase separation is very difficult to perform within a reasonable amount of time, particularly when the phases are mixed as an emulsion. In such cases, according to some embodiments, de-emulsifying additives can be injected into the flow line using dosing pump system 152. The amount of de-emulsifier is typically relatively small, on the order of several ppm. As will be described in further detail infra, dosing pump system 152 is configured to continuously inject the de-emulsifying agent into the flow line at controlled quantities and rates. The dosing pump system 152 is configured to inject the fluid at high pressures, for example at the fluid pressure of wellhead 110, while being robust enough to withstand the deep-sea environment.

Figure 2:
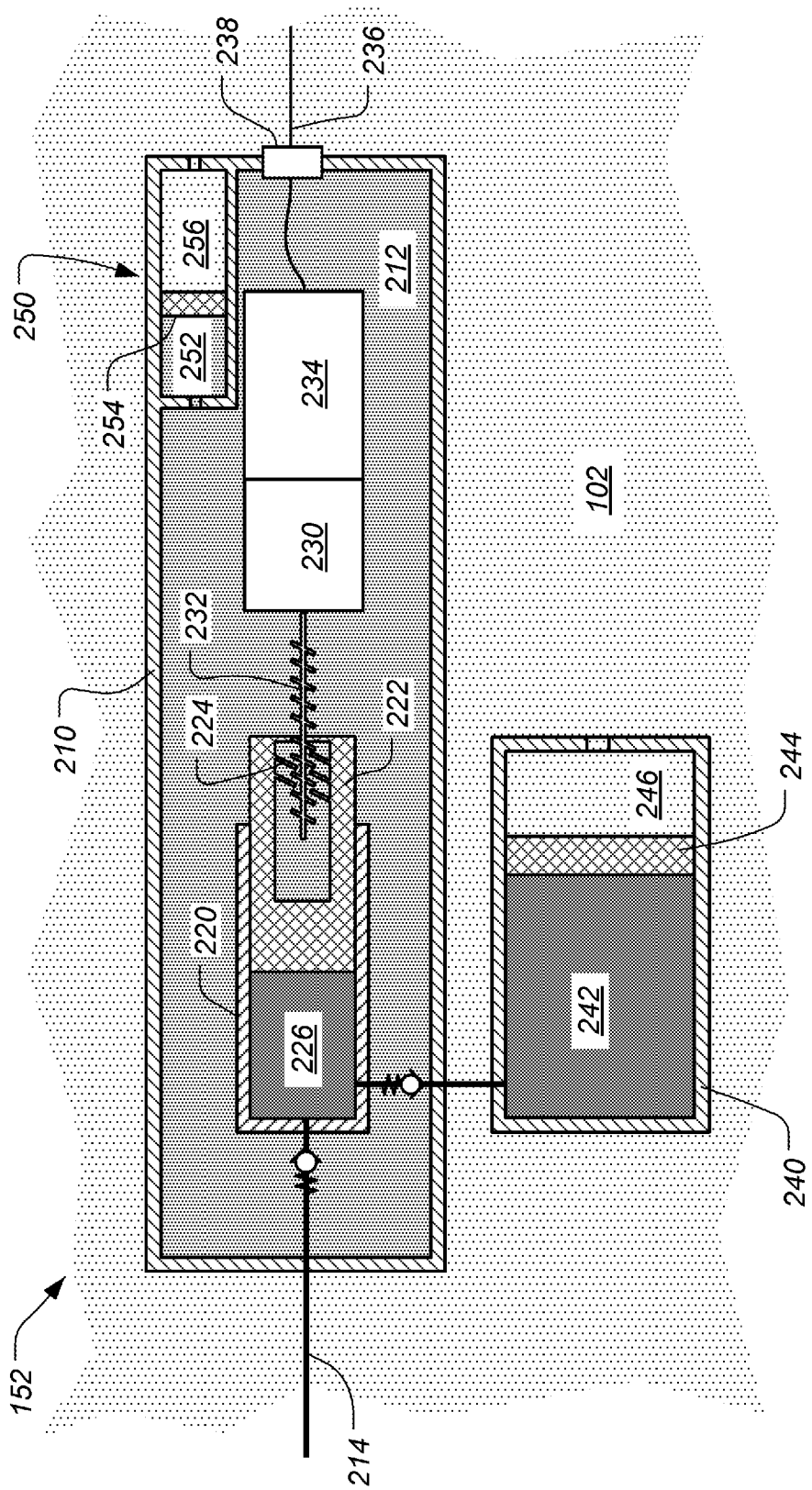
FIG. 2 is a diagram illustrating further details of a pressure-compensated subsea dosing pump system, according to some embodiments.

FIG. 2 is a diagram illustrating further details of a pressure-compensated subsea dosing pump system, according to some embodiments. The dosing pump system 152 includes a housing 210 that houses the syringe-type pump, motor and pump drive mechanism. The pump made up of cylinder 220 into which high pressure piston 222 slides. An interior volume 226, defined by cylinder 220 and piston 222, can be filled with the injection fluid from reservoir 240 via a check valve as shown. The piston 222 fits tightly within cylinder 220 and can use one or more seals to ensure that none of the injection fluid leaks into the interior region 212 of the housing 210. The reservoir 240 includes a compensating piston 244 that moves to change the volume 242 of the reservoir 240 as needed. Note the right side volume 246 of reservoir 240 is open to the seawater 102 via one or more ports. The pump is driven by a stepper motor 234 and a reducing gear box 230 that rotates the screw 232 that engages teeth on a non-rotating element 224 that pushes on piston 222. The motor 234 is powered and controlled via wires 236 that pass through the housing 210 via feed through 238. Wires 236 lead to a motor driver (not shown). The housing 210 is also pressure compensated to the pressure of seawater 102, using pressure compensator 250 which includes a compensating piston 254 that separates two volumes 252 and 256. The interior region 212 of housing 210 and volume 252 of the pressure compensator 250 are filled with a non-compressible fluid such as oil. The volume 256 of pressure compensator 250 is open to the seawater 102 via one or more ports. Through the use of the pressure compensator 250 and the compensating piston 244, the system 152 can be automatically pressure compensated due to the environmental pressure as well as due to temperature changes.

According to some embodiments non-rotating element 224 uses ball bearings instead of teeth to form a ball screw actuator instead of a lead screw actuator for accepting greater axial loads. According to some embodiments, the non-rotating element 224 and piston 222 are formed as a single part. Although not visible in FIG. 2, according to other embodiments, non-rotating element 224 and piston 222 are formed of separate parts. Since the piston 222 is in a cylindrical bore, the driven, non-rotating element 224 should be mechanically stabilized so as to prevent rotation when pushing and/or pulling the piston 222.

The pump system 152 is actuated by moving the piston 224 back and forth with the screw 232 and the stepper motor 234. The rate and quantity of injected fluid are accurately set by the stepper motor 234 and its driver controlled by a user on the surface through a computer and communication line. The injected fluid flows through injection line 214 to the fluid flow line, such as production flow line where multiphase production fluid is flowing. According to some embodiments, using a design shown in FIGS. 2 and 3 the pumping system 152 can be configured to accurately and controllably inject fluid into a high pressure flow line at rates of less than 10 millilitres per minute. Note that the motor and pump are protected from the sea environment by the housing 210, which can be made relatively thin and light due to the pressure compensation provided.

Figure 3:
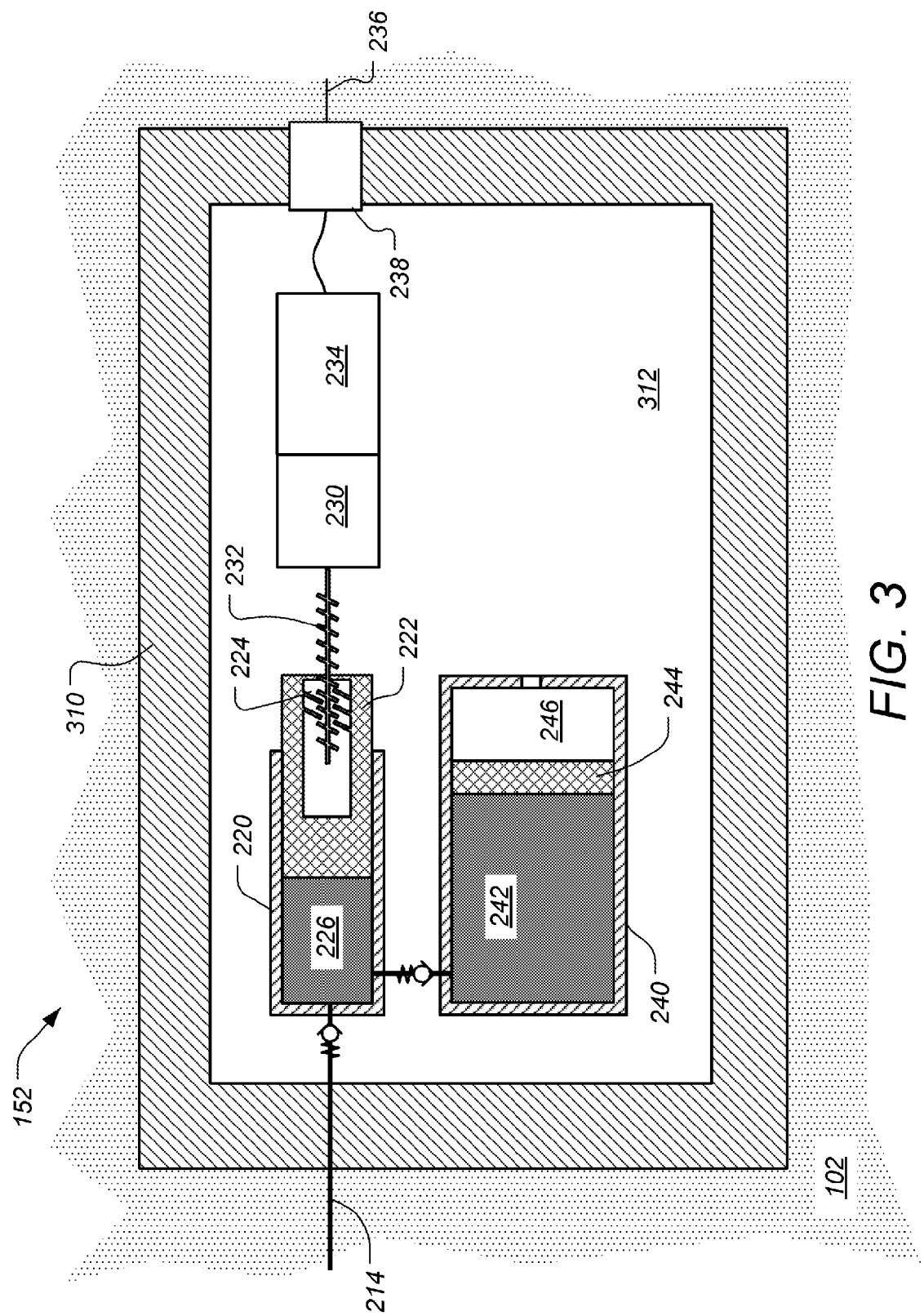
FIG. 3 is a diagram illustrating further details of a pressurized subsea dosing pump system, according to some embodiments.

FIG. 3 is a diagram illustrating further details of a pressurized subsea dosing pump system, according to some embodiments. In the case of FIG. 3, the subsea dosing pump 152 is configured to remain at lower pressures (e.g. at or near atmospheric pressure) throughout deployment to the subsea location. Many of the components are the same or similar to the system shown in FIG. 2. The housing 310 is made of a considerably thicker material than the case shown in FIG. 2, and according to some embodiments, the reservoir 240 is included within the housing 310. The interior region 312 of housing 310 is thus air instead of oil, as in the case of region 212 of FIG. 2.

Although the embodiments described supra are in the context of injecting a de-emulsifying fluid into flow line for purposes of aiding phase separation for sampling, the techniques are equally applicable to other subsea applications. According to some embodiments, the dosing pump system 152 is used for injecting marker substances for purposes of fluid flow measurement (e.g. a time of flight measurement). According to other embodiments, the dosing pump system 152 is used for injecting small quantities of fluid for chemical properties' analysis purposes (e.g. injecting a re-agent for in-situ chemical analsysis).

It is noted that the foregoing examples have been provided merely for the purpose of explanation and are in no way to be construed as limiting of the present invention. While the present invention has been described with reference to exemplary embodiments, it is understood that the words, which have been used herein, are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

The invention claimed is:

1. A subsea deployable pumping system comprising:
a housing configured to be deployed in a subsea environment, the housing including an interior region filled with a liquid;
a pump disposed within the interior region of the housing, the pump being configured to inject an injection fluid through an injection port;
a motor disposed within the interior region of the housing and configured to drive said pump and cause the pump to inject said injection fluid, said pump and motor being configured to inject said injection fluid at a controllable rate of less than 10 milliliters per minute;
a reservoir in fluid communication with said pump, configured to contain a volume of said injection fluid and to supply said injection fluid to said pump; and
a pressure compensator configured to match pressure of the liquid in the interior region of the housing with seawater pressure outside the housing.

2. A system according to claim 1 wherein said pump comprises:
a cylindrical cavity in fluid communication with the injection port and the reservoir, wherein the cylindrical cavity is disposed within the interior region of the housing; and
a plunger configured to fit tightly within the cylindrical cavity such that injection fluid within the cylindrical cavity is forced through said injection port when the plunger is driven in a longitudinal direction by said motor.

3. A system according to claim 2 wherein said motor comprises a stepper motor configured to controllably rotate a drive shaft; and
wherein the system further comprises a driving linkage coupled to the motor and configured to drive said plunger in the longitudinal direction through said cylindrical cavity.

4. A system according to claim 3 wherein said driving linkage comprises:
a screw shaft configured to engage a non-rotating element that pushes said piston; and
a gear system configured to allow said screw to be rotationally driven by said stepper motor through the drive shaft.

5. A system according to claim 4 wherein said screw shaft engages teeth on said non-rotating element.

6. A system according to claim 4 wherein said screw shaft engages a plurality of ball bearings within said non-rotating element.

7. A system according to claim 2 wherein the pump and motor are configured to inject the injection fluid at pressures of at least 1000 psi.

8. A system according to claim 1 wherein the liquid filling the interior region of the housing is an oil, and the pressure compensator includes a piston separating two volumes one of which is open to seawater outside the housing and another of which is open to the interior region.

9. A system according claim 1 wherein the reservoir includes a pressure compensation mechanism configured to match pressure of the injection fluid within the reservoir with seawater pressure outside the housing.

10. A system according to claim 1 wherein the subsea deployable pumping system is configured to be deployable using a remotely operated underwater vehicle (ROV).

11. A subsea deployable pumping system comprising:
a housing configured to be deployed in a subsea environment, the housing including an interior region filled with oil;
a reservoir configured to contain a volume of injection fluid;
a cylindrical cavity disposed within the interior region of the housing in fluid communication with an injection port and with said reservoir;
a plunger disposed within the interior region of the housing and configured to fit tightly within the cylindrical cavity such that injection fluid in the cylindrical cavity is forced through said injection port when the plunger is driven in a longitudinal direction;

a motor disposed within the interior region of the housing and configured to drive said plunger in the longitudinal direction thereby injecting said injection fluid through said injection port; and a pressure compensator configured to match pressure of the oil in the interior region of the housing with seawater pressure outside the housing.

12. A system according to claim 11 wherein said motor comprises a stepper motor; wherein system further comprises:

a drive shaft coupled to the stepper motor, wherein the stepper motor is configured to controllable rotate the drive shaft; and a driving linkage configured to drive said plunger in the longitudinal direction through said cylindrical cavity through rotation of the drive shaft.

13. A system according to claim 12 wherein said driving linkage comprises:

a screw configured to engage a non-rotating element that pushes and pulls said piston; and a gear system configured to allow said screw to be rotationally driven by said stepper motor through the drive shaft.

14. A system according to claim 11 wherein said cylindrical cavity, plunger and motor are configured to inject said injection fluid at a controllable rate of less than 10 milliliters per minute.

15. A system according claim 11 wherein the reservoir includes a pressure compensation mechanism configured to match pressure of the injection fluid within the reservoir with seawater pressure outside the housing.

16. A system according to claim 11 wherein the housing is configured to maintain near atmospheric pressure within the interior region of the housing while the exterior of said housing is exposed to subsea pressures.

17. A system according to claim 11 wherein the subsea deployable pumping system is configured to be deployable using a remotely operated underwater vehicle (ROV).

18. A system according to claim 11 wherein the pressure compensator includes a piston separating two volumes one of which is open to seawater outside the housing and another of which is open to the interior region.

19. A method of injecting small volumes of an injection fluid into a subsea flow line carrying a fluid, the method comprising:

deploying a pumping system to a subsea location where the subsea flow line is used to carry a flowing fluid, wherein the pumping system comprises:

a housing configured to be deployed in a subsea environment, the housing including an interior region filled with a liquid;

a pump disposed within the interior region of the housing; and a motor disposed within the interior region of the housing;

injecting the injection fluid into the subsea flow line using the motor to drive the pump from within the interior region of the housing, the injection fluid being injected at a rate of less than 10 milliliters per minute; and matching the pressure of the liquid in the interior region of the housing with seawater pressure outside the housing with a pressure compensator.

20. A method according to claim 19 wherein the pumping system further comprises:

a reservoir configured to contain a volume of the injection fluid; and wherein the pump further comprises:

a cylindrical cavity disposed within the housing in fluid communication with said reservoir and with an injection port configured to be attached to said flow line; and a plunger disposed within the housing configured to fit tightly within the cylindrical cavity such that injection fluid in the cylindrical cavity is forced through said injection port and into the flow line when the plunger is driven in a longitudinal direction.

21. A method according to claim 19 wherein the fluid is a hydrocarbon bearing production fluid extracted from a subterranean rock formation.

22. A method according to claim 21 wherein the production fluid is a multiphase fluid, the injection fluid is a de-emulsifying agent and said method further comprising:

separating a desired phase of the multiphase fluid at least in part aided by the injection of the de-emulsifying agent; and obtaining a sample of the desired phase of the multiphase fluid.

23. A method according to claim 21 wherein the injection fluid is an additive used for a type of in-situ analysis of the production fluid selected from a group consisting of: flow rate analysis by time of flight measurement; and chemical analysis aided by a re-agent additive.

24. A method according to claim 19 wherein the said deploying of the pumping system is carried out by a remotely operated underwater vehicle (ROV).

25. A method according to claim 19 wherein matching the pressure of the liquid in the interior region of the housing comprises moving a piston that separates two volumes, one of which is open to seawater outside the housing and another of which his open to the interior region.

* * * * *